US008611977B2

(12) United States Patent
Baker, Jr.

(10) Patent No.: US 8,611,977 B2
(45) Date of Patent: Dec. 17, 2013

(54) METHOD AND APPARATUS FOR OPTICAL DETECTION OF MIXED VENOUS AND ARTERIAL BLOOD PULSATION IN TISSUE

(75) Inventor: Clark R. Baker, Jr., Castro Valley, CA (US)

(73) Assignee: Covidien LP, Mansfield, MA (US)

( * ) Notice: Subject to any disclaimer, the term of this patent is extended or adjusted under 35 U.S.C. 154(b) by 2384 days.

(21) Appl. No.: 10/796,584

(22) Filed: Mar. 8, 2004

(65) Prior Publication Data

US 2005/0197579 A1    Sep. 8, 2005

(51) Int. Cl.
*A61B 5/1455* (2006.01)
*A61B 5/02* (2006.01)

(52) U.S. Cl.
USPC .......................................... 600/323; 600/500

(58) Field of Classification Search
USPC .......... 600/473, 407, 310, 330, 336, 322–323
See application file for complete search history.

(56) References Cited

U.S. PATENT DOCUMENTS

| | | |
|---|---|---|
| 3,638,640 A | 2/1972 | Shaw |
| 4,854,699 A | 8/1989 | Edgar, Jr. |
| 4,911,167 A | 3/1990 | Corenman et al. |
| 4,936,679 A | 6/1990 | Mersch |
| 4,960,126 A | 10/1990 | Conlon |
| 4,971,062 A | 11/1990 | Hasebe et al. |
| 4,974,591 A | 12/1990 | Awazu et al. |
| 5,025,791 A | 6/1991 | Niwa |
| 5,028,787 A | 7/1991 | Rosenthal et al. |
| 5,065,749 A | 11/1991 | Hasebe et al. |
| 5,084,327 A | 1/1992 | Stengel |
| 5,275,159 A | 1/1994 | Griebel |
| 5,285,783 A | 2/1994 | Secker |
| 5,368,026 A * | 11/1994 | Swedlow et al. ............. 600/323 |
| 5,413,100 A | 5/1995 | Barthelemy |
| 5,483,646 A | 1/1996 | Uchikoga |
| 5,503,148 A * | 4/1996 | Pologe et al. ................. 600/323 |
| 5,645,059 A | 7/1997 | Fein et al. |
| 5,662,106 A * | 9/1997 | Swedlow et al. ............. 600/331 |
| 5,730,124 A | 3/1998 | Yamauchi |
| 5,779,631 A | 7/1998 | Chance |
| 5,817,008 A | 10/1998 | Rafert |
| 5,830,135 A | 11/1998 | Bosque |
| 5,830,139 A | 11/1998 | Abreu |

(Continued)

FOREIGN PATENT DOCUMENTS

| | | |
|---|---|---|
| DE | 69123448 | 5/1997 |
| JP | 24148070 | 5/2004 |

(Continued)

OTHER PUBLICATIONS

Masimo, Technical Bulletin 1, "Discrete Saturation Transform" (2006), pp. 4-5.*

(Continued)

*Primary Examiner* — Eric Winakur

(57) ABSTRACT

A method and device for detecting the presence of mixed venous and arterial blood pulsation in tissue, including receiving first and second electromagnetic radiation signals from a blood perfused tissue portion corresponding to infrared and red wavelengths of light, obtaining a measure of a phase difference between the first and second electromagnetic radiation signals, comparing the measure with a threshold value to form a comparison, and detecting the presence or absence of venous pulsation using the comparison.

18 Claims, 3 Drawing Sheets

(56) References Cited

U.S. PATENT DOCUMENTS

| | | |
|---|---|---|
| 5,831,598 A | 11/1998 | Kauffert et al. |
| 5,853,364 A | 12/1998 | Baker, Jr. et al. |
| 5,871,442 A | 2/1999 | Madarasz et al. |
| 5,873,821 A | 2/1999 | Chance et al. |
| 6,018,673 A * | 1/2000 | Chin et al. .................. 600/322 |
| 6,081,742 A | 6/2000 | Amano et al. |
| 6,120,460 A | 9/2000 | Abreu |
| 6,134,460 A | 10/2000 | Chance |
| 6,151,516 A | 11/2000 | Kiani-Azarbayjany et al. |
| 6,222,189 B1 | 4/2001 | Misner |
| 6,285,895 B1 | 9/2001 | Ristolainen et al. |
| 6,312,393 B1 | 11/2001 | Abreu |
| 6,353,750 B1 | 3/2002 | Kimura et al. |
| 6,415,236 B2 | 7/2002 | Kobayashi et al. |
| 6,419,671 B1 | 7/2002 | Lemberg |
| 6,438,399 B1 | 8/2002 | Kurth |
| 6,449,501 B1 | 9/2002 | Reuss |
| 6,461,305 B1 | 10/2002 | Schnall |
| 6,480,729 B2 | 11/2002 | Stone |
| 6,487,439 B1 | 11/2002 | Skladnev et al. |
| 6,544,193 B2 | 4/2003 | Abreu |
| 6,549,795 B1 | 4/2003 | Chance |
| 6,591,122 B2 | 7/2003 | Schmitt |
| 6,606,509 B2 | 8/2003 | Schmitt |
| 6,618,042 B1 | 9/2003 | Powell |
| 6,622,095 B2 | 9/2003 | Kobayashi et al. |
| 6,662,030 B2 | 12/2003 | Khalil et al. |
| 6,675,029 B2 | 1/2004 | Monfre et al. |
| 6,687,519 B2 | 2/2004 | Steuer et al. |
| 6,690,958 B1 | 2/2004 | Walker et al. |
| 6,714,245 B1 | 3/2004 | Ono |
| 6,731,274 B2 | 5/2004 | Powell |
| 6,754,515 B1 | 6/2004 | Pologe |
| 6,785,568 B2 | 8/2004 | Chance |
| 6,793,654 B2 | 9/2004 | Lemberg |
| 6,819,950 B2 | 11/2004 | Mills |
| 6,850,053 B2 | 2/2005 | Daalmans et al. |
| 6,869,402 B2 | 3/2005 | Arnold |
| 6,879,850 B2 * | 4/2005 | Kimball .................. 600/336 |
| 6,898,451 B2 | 5/2005 | Wuori |
| 6,947,781 B2 | 9/2005 | Asada |
| 6,949,081 B1 | 9/2005 | Chance |
| 6,970,792 B1 * | 11/2005 | Diab .................. 600/323 |
| 6,987,994 B1 * | 1/2006 | Mortz .................. 600/336 |
| 6,993,372 B2 | 1/2006 | Fine |
| 6,996,427 B2 | 2/2006 | Ali |
| 7,024,233 B2 | 4/2006 | Ali |
| 7,035,697 B1 | 4/2006 | Brown |
| 7,041,063 B2 | 5/2006 | Abreu |
| 7,043,289 B2 | 5/2006 | Fine et al. |
| 7,044,917 B2 | 5/2006 | Arnold |
| 7,065,392 B2 | 6/2006 | Kato |
| 7,095,491 B2 | 8/2006 | Forstner et al. |
| 7,206,621 B2 | 4/2007 | Aoyagi et al. |
| 7,236,811 B2 | 6/2007 | Schmitt |
| 7,239,902 B2 | 7/2007 | Schmitt et al. |
| 7,263,395 B2 | 8/2007 | Chan |
| 7,272,426 B2 | 9/2007 | Schmid |
| 7,366,569 B2 | 4/2008 | Belalcazar |
| 7,469,157 B2 | 12/2008 | Diab |
| 7,469,158 B2 | 12/2008 | Cutler et al. |
| 7,534,212 B2 | 5/2009 | Baker, Jr. |
| 7,551,950 B2 | 6/2009 | Cheng |
| 7,621,877 B2 | 11/2009 | Schnall |
| 2002/0042558 A1 | 4/2002 | Mendelson |
| 2002/0103423 A1 | 8/2002 | Chin et al. |
| 2002/0156354 A1 | 10/2002 | Larson |
| 2002/0198443 A1 | 12/2002 | Ting |
| 2003/0023140 A1 | 1/2003 | Chance |
| 2003/0036689 A1 | 2/2003 | Diab et al. |
| 2004/0171920 A1 | 9/2004 | Mannheimer et al. |
| 2005/0113651 A1 | 5/2005 | Wood et al. |
| 2005/0113656 A1 | 5/2005 | Chance |
| 2005/0192488 A1 | 9/2005 | Bryenton et al. |
| 2005/0228248 A1 | 10/2005 | Dietiker |
| 2006/0020181 A1 | 1/2006 | Schmitt |
| 2006/0189872 A1 | 8/2006 | Arnold |
| 2006/0195025 A1 | 8/2006 | Ali |
| 2006/0247501 A1 | 11/2006 | Ali |
| 2008/0009689 A1 | 1/2008 | Benaron |

FOREIGN PATENT DOCUMENTS

| | | |
|---|---|---|
| JP | 24166775 | 6/2004 |
| JP | 25046234 | 2/2005 |
| JP | 25095606 | 4/2005 |
| JP | 25169020 | 6/2005 |
| JP | 3944448 | 7/2007 |
| JP | 4038280 | 1/2008 |
| WO | WO9200513 | 1/1992 |
| WO | WO03039326 | 5/2003 |
| WO | WO03063697 | 8/2003 |
| WO | WO2004006748 | 1/2004 |

OTHER PUBLICATIONS

Aoyagi, T., et al.; "Analysis of Motion Artifacts in Pulse Oximetry," Japanese Society ME, vol. 42, p. 20 (1993) (Article in Japanese—contains English summary of article).

Goldman, Julian M.; "Masimo Signal Extraction Pulse Oximetry," Journal of Clinical Monitoring and Computing, vol. 16, pp. 475-483 (2000).

Yamazaki, Nakaji, et al.; "Motion Artifact Resistant Pulse Oximeter (Durapulse PA 2100)," Journal of Oral Cavity Medicine, vol. 69, No. 4, pp. 53 (date unknown) (Article in Japanese—contains English summary of article).

PCT International Search Report mailed Jun. 15, 2005; PCT/US2005/007407, 9 pages.

* cited by examiner

Venous Pulsation During Normoxia in Trendelenberg Position:
In House Test 8/20/2002

METHOD AND APPARATUS FOR OPTICAL DETECTION OF MIXED VENOUS AND ARTERIAL BLOOD PULSATION IN TISSUE

BACKGROUND OF THE INVENTION

The present invention relates in general to pulse oximetry, and in particular to the processing of signals generated by a pulse oximeter.

A pulse oximeter is typically used to measure various blood characteristics including the blood oxygen saturation of hemoglobin in arterial blood and the pulse rate of the patient. Measurement of these characteristics has been accomplished by use of a non-invasive sensor that passes light through a portion of a patient's blood perfused tissue and photo-electrically senses the absorption and scattering of light in such tissue. The amount of light absorbed and scattered is then used to estimate the amount of blood constituent in the tissue using various algorithms known in the art. The "pulse" in pulse oximetry comes from the time varying amount of arterial blood in the tissue during a cardiac cycle. The signal processed from the sensed optical measurement is the familiar plethysmographic waveform, which corresponds with the cyclic attenuation of optical energy through a portion of a patient's blood perfused tissue.

Various physiological and/or external factors can adversely impact the accuracy and/or the reliability of physiological parameters that are estimated by a pulse oximeter. These undesirable factors are sometimes referred to as artifacts. Venous pulsation is one undesired artifact in pulse oximetry, and may be caused by a patient's medical condition.

It is therefore desirable that a pulse oximetry system be designed which effectively and accurately detects and/or notifies a clinician of the presence of venous pulsation.

BRIEF SUMMARY OF THE INVENTION

The present invention provides a pulse oximeter that has the capability of detecting the presence of venous blood pulsation, or the presence of mixed venous and arterial blood pulsation in tissue.

In one embodiment, the present invention provides a method of detecting the presence of mixed venous and arterial blood pulsation in tissue. The method includes receiving first and second electromagnetic radiation signals from a blood perfused tissue portion corresponding to infrared and red wavelengths of light; obtaining a measure of a phase difference between the first and second electromagnetic radiation signals; comparing the measure with a threshold value to form a comparison; and detecting the presence or absence of venous pulsation using the comparison.

In one aspect, the measure of a phase difference between the first and second electromagnetic radiation signals is a measure of a persistent phase difference between the first and second electromagnetic radiation signals.

In another aspect, the measure of a phase difference is a measure of the openness of an ellipse on a Lissajous plot formed by comparing the first electromagnetic radiation signal against the second electromagnetic radiation signal.

In another embodiment, the present invention provides a device for detecting the presence of mixed venous and arterial blood pulsation in tissue. The device includes a module for receiving first and second electromagnetic radiation signals from a blood perfused tissue portion corresponding to infrared and red wavelengths of light; a module for obtaining a measure of a phase difference between the first and second electromagnetic radiation signals; a module for comparing the measure with a threshold value to form a comparison; and a module for detecting the presence or absence of venous pulsation using the comparison.

For a fuller understanding of the nature and advantages of the embodiments of the present invention, reference should be made to the following detailed description taken in conjunction with the accompanying drawings.

DETAILED DESCRIPTION OF THE INVENTION

The methods and systems in accordance with the embodiments of the present invention are directed towards detecting the presence or absence of venous or mixed venous and arterial pulsation in a blood perfused tissue. The invention is particularly applicable to and will be explained by reference to measurements of oxygen saturation of hemoglobin in arterial blood and pulse or heart rate, as in pulse oximeter monitors and pulse oximetry sensors.

A typical pulse oximeter measures two physiological parameters, percent oxygen saturation of arterial blood hemoglobin ($SpO_2$ or sat) and pulse rate. Oxygen saturation can be estimated using various techniques. In one common technique, the photocurrent generated by the photo-detector is conditioned and processed to determine the ratio of modulation ratios (ratio of ratios) of the red to infrared (IR) signals. This modulation ratio has been observed to correlate well to arterial oxygen saturation. Pulse oximeters and sensors may be empirically calibrated by measuring the modulation ratio over a range of in vivo measured arterial oxygen saturations ($SaO_2$) on a set of patients, healthy volunteers, or animals. The observed correlation is used in an inverse manner to estimate blood oxygen saturation ($SpO_2$) based on the measured value of modulation ratios of a patient. The estimation of oxygen saturation using modulation ratios is described in U.S. Pat. No. 5,853,364, entitled "METHOD AND APPARATUS FOR ESTIMATING PHYSIOLOGICAL PARAMETERS USING MODEL-BASED ADAPTIVE FILTERING," issued Dec. 29, 1998, and U.S. Pat. No. 4,911,167, entitled "METHOD AND APPARATUS FOR DETECTING OPTICAL PULSES," issued Mar. 27, 1990, which are both herein incorporated by reference in their entirety for all purposes. The relationship between oxygen saturation and modulation ratio is described, for example, in U.S. Pat. No. 5,645,059, entitled "MEDICAL SENSOR WITH MODULATED ENCODING SCHEME," issued Jul. 8, 1997, which is herein incorporated by reference in its entirety for all purposes. Most pulse oximeters extract the plethysmographic signal having first determined saturation or pulse rate, both of which are susceptible to interference.

Figure 1:
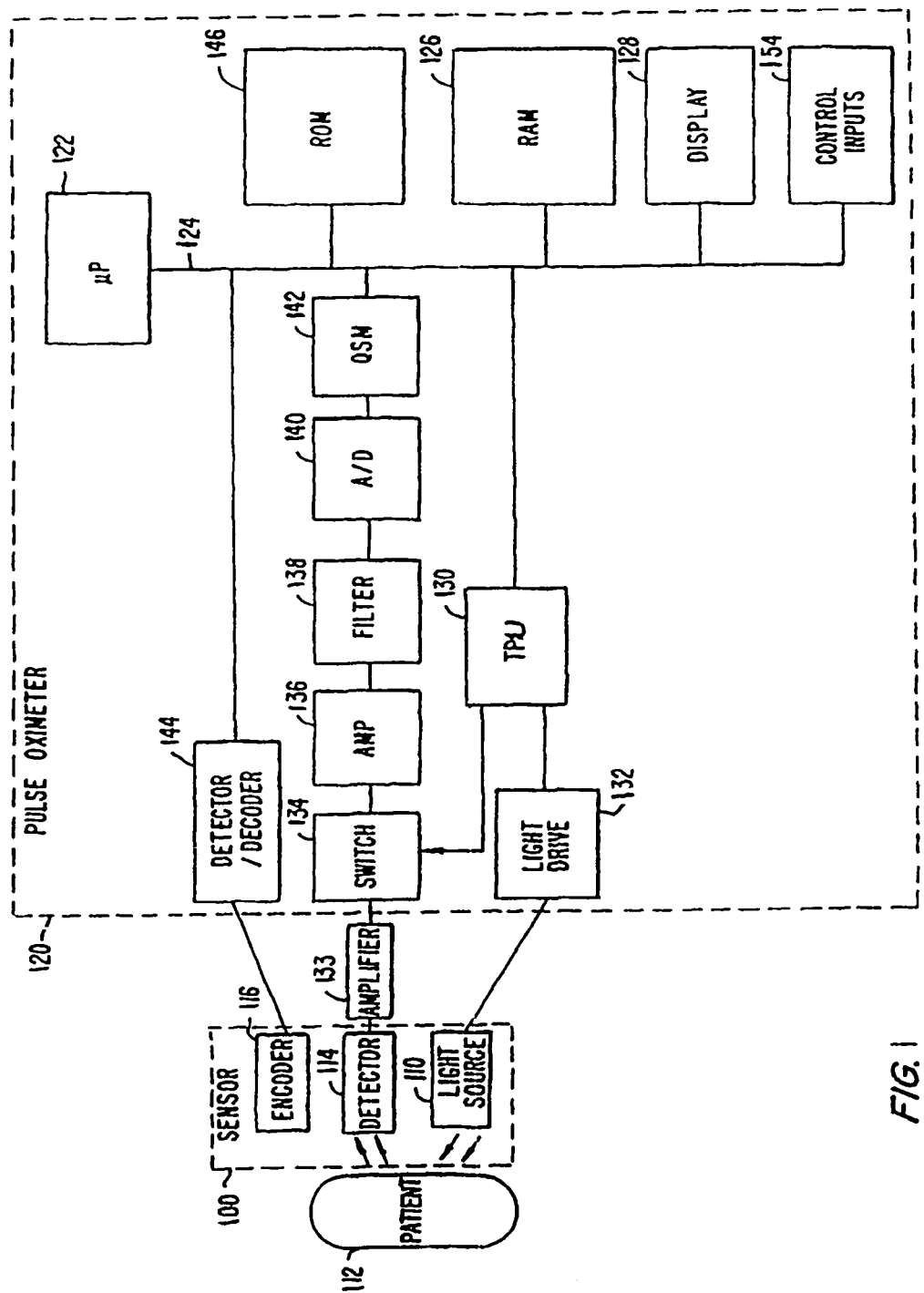
FIG. 1 is a block diagram of an exemplary oximeter.

FIG. 1 is a block diagram of one embodiment of a pulse oximeter that may be configured to implement the embodiments of the present invention. The venous pulsation detection embodiments of the present invention may be implemented as a data processing algorithm that is executed by the microprocessor 122, described below. Light from light source 110 passes into a blood perfused tissue 112, and is scattered and detected by photodetector 114. A sensor 100 containing the light source and photodetector may also contain an encoder 116 which provides signals indicative of the wavelength of light source 110 to allow the oximeter to select appropriate calibration coefficients for calculating oxygen saturation. Encoder 116 may, for instance, be a resistor.

Sensor 100 is connected to a pulse oximeter 120. The oximeter includes a microprocessor 122 connected to an internal bus 124. Also connected to the bus is a RAM memory 126 and a display 128. A time processing unit (TPU) 130 provides timing control signals to light drive circuitry 132 which controls when light source 110 is illuminated, and if multiple light sources are used, the multiplexed timing for the different light sources. TPU 130 also controls the gating-in of signals from photodetector 114 through an amplifier 133 and a switching circuit 134. These signals are sampled at the proper time, depending upon which of multiple light sources is illuminated, if multiple light sources are used. The received signal is passed through an amplifier 136, a low pass filter 138, and an analog-to-digital converter 140. The digital data is then stored in a queued serial module (QSM) 142, for later downloading to RAM 126 as QSM 142 fills up. In one embodiment, there may be multiple parallel paths of separate amplifier, filter and A/D converters for multiple light wavelengths or spectra received.

Based on the value of the received signals corresponding to the light received by photodetector 114, microprocessor 122 will calculate the oxygen saturation using various algorithms. These algorithms require coefficients, which may be empirically determined, corresponding to, for example, the wavelengths of light used. These are stored in a ROM 146. In a two-wavelength system, the particular set of coefficients chosen for any pair of wavelength spectra is determined by the value indicated by encoder 116 corresponding to a particular light source in a particular sensor 100. In one embodiment, multiple resistor values may be assigned to select different sets of coefficients. In another embodiment, the same resistors are used to select from among the coefficients appropriate for an infrared source paired with either a near red source or far red source. The selection between whether the near red or far red set will be chosen can be selected with a control input from control inputs 154. Control inputs 154 may be, for instance, a switch on the pulse oximeter, a keyboard, or a port providing instructions from a remote host computer. Furthermore, any number of methods or algorithms may be used to determine a patient's pulse rate, oxygen saturation or any other desired physiological parameter.

The brief description of an exemplary pulse oximeter set forth above, serves as a basis for describing the methods for detecting the presence of venous pulsation, which are described below. The embodiments of the present invention, which are used to detect and/or indicate the presence of venous pulsation or mixed venous and arterial pulsation are described below in conjunction with the block diagram of FIG. 2.

Figure 2:
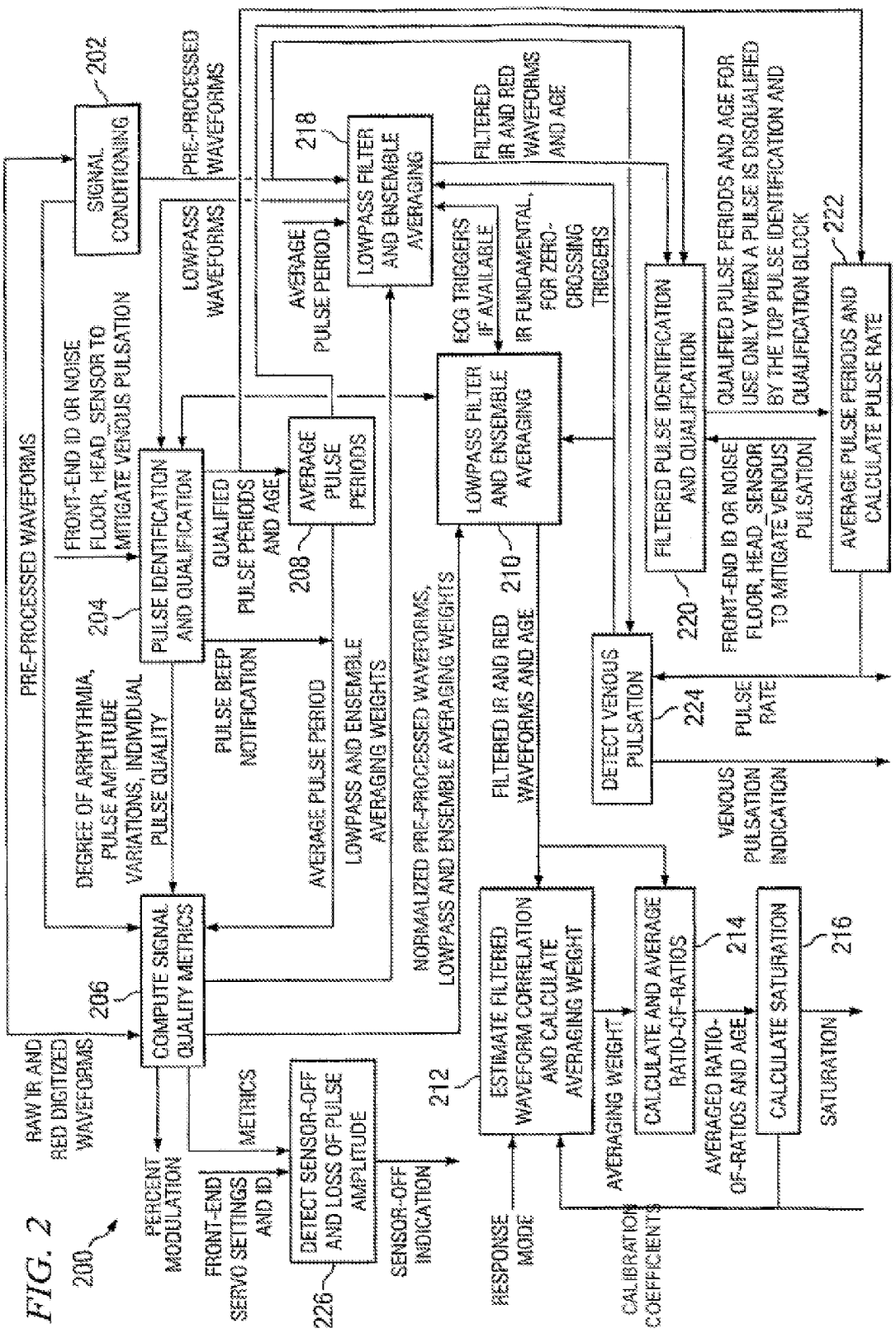
FIG. 2 is a block diagram of the signal processing architecture of a pulse oximeter in accordance with one embodiment of the present invention.

The embodiments of the present invention may be implemented as a part of a larger signal processing system used to process optical signals for the purposes of operating a pulse oximeter. Such a signal processing system is shown in FIG. 2, which is a block diagram 200 of a signal processing architecture of a pulse oximeter in accordance with one embodiment of the present invention. The signal processing architecture 200 in accordance with the embodiments of the present invention may be implemented as a software algorithm that is executed by a processor of a pulse oximeter. In addition to calculating oxygen saturation and pulse rate, the system 200 measures various signal metrics that are used to determine filter weighting coefficients. Signal metrics are things that indicate if a pulse is likely a plethysmograph or noise. Signal metrics may be related to, for example, frequency (is it in the range of a human heart rate), shape (is it shaped like a cardiac pulse), rise time, etc. The system shown in FIG. 2 calculates both the oxygen saturation, and the pulse rate, as well as detecting venous pulsation and sensor off and lost pulse conditions, which are described separately below.

I. Oxygen Saturation Calculation

Block 202 represents the operation of the Signal Conditioning block. The digitized red and IR signals or waveforms are received and are conditioned in this block by: (1) taking the $1^{st}$ derivative to get rid of baseline shift, (2) low pass filtering with fixed coefficients, and (3) dividing by a DC value to preserve the ratio. The function of the Signal Conditioning subsystem is to emphasize the higher frequencies that occur in the human plethysmograph and to attenuate low frequencies in which motion artifact is usually concentrated. The Signal Conditioning subsystem selects its filter coefficients (wide or narrow band) based on hardware characteristics identified during initialization. Inputs to block 202 are digitized red and IR signals, and its outputs are pre-processed red and IR signals.

Block 204 represents the operation of the Pulse Identification and Qualification block. The low pass filtered digitized red and IR signals are provided to this block to identify pulses, and qualify them as likely arterial pulses. This is done using a pre-trained neural network, and is primarily done on the IR signal. The pulse is identified by examining its amplitude, shape and frequency. An input to this block is the average pulse period from block 208. This function changes the upfront qualification using the pulse rate. The output of block 204 indicates the degree of arrhythmia and individual pulse quality. Inputs to block 204 are: (1) pre-processed red and IR signals, (2) Average pulse period, and (3) lowpass waveforms from the low pass filter. Outputs from block 204 include: (1) degree of arrhythmia, (2) pulse amplitude variations, (3) individual pulse quality, (4) pulse beep notification, and (5) qualified pulse periods and age.

Block 206 is used to compute signal quality metrics. This block (block 206) determines the pulse shape (e.g., derivative skew), period variability, pulse amplitude and variability, Ratio of Ratios variability, and frequency content relative to pulse rate. Inputs to block 206 include: (1) raw digitized red and IR signals, (2) degree of arrhythmia, individual pulse quality, pulse amplitude variation, (3) pre-processed red and IR signals, and (4) average pulse period. Outputs from block 206 include: (1) lowpass and ensemble averaging filter weights, (2) metrics for sensor off detector, (3) normalized pre-processed waveforms, and (4) percent modulation.

Block 208 computes average pulse periods. This block (block 208) calculates the average pulse period from the pulses received. Inputs to block 208 include: qualified pulse periods and age. An output from block 208 includes the average pulse period.

Block 210 represents the functioning of the lowpass filter and ensemble averaging subsystem. Block 210 low pass filters and ensemble averages normalized and preprocessed waveforms processed by block 206. The weights for the low pass filter are determined by the Signal Metrics block 206.

The signal is also ensemble averaged (this attenuates frequencies other than those of interest near the pulse rate and its harmonics), with the ensemble averaging filter weights also determined by Signal Metrics block 206. Less weight is assigned if the signal is flagged as degraded. More weight is assigned if the signal is flagged as arrhythmic because ensemble-averaging is not appropriate during arrhythmia. Red and IR waveforms are processed separately, but with the same filtering weights. The filtering is delayed (e.g., approximately one second) to allow the signal metrics to be calculated first.

The filters use continuously variable weights. If samples are not to be ensemble-averaged, then the weighting for the previous filtered samples is set to zero in the weighted average, and the new samples are still processed through the signal processing algorithm. This block tracks the age of the signal and/or the accumulated amount of filtering (e.g., sum of response times and delays in processing). Too old a result will be flagged, if good pulses haven't been detected for a while. The inputs to block 210 include: (1) normalized pre-processed red and IR signals, (2) average pulse period, (3) low pass filter weights and ensemble averaging filter weights, (4) ECG triggers, if available, and (5) IR fundamental, for zero-crossing triggers. Outputs from block 210 include: (1) filtered red and IR signals, and (2) age.

Block 212 represents operations that estimate the ratio-of-ratios variance for the filtered waveforms and calculate averaging weights. The variable weighting for the filter is controlled by the ratio-of-ratios variance. The effect of this variable-weight filtering is that the ratio-of-ratios changes slowly as artifact increases and changes quickly as artifact decreases. The subsystem has two response modes, including fast and normal modes. For example, filtering in the fast mode targets an age metric of 3 seconds, and the target age may be 5 seconds in the normal mode. In the fast mode, the minimum weighting of the current value is clipped at a higher level. In other words, a low weight is assigned to the newest ratio-of-ratios calculation if there is noise present, and a high weight if no noise is present. The inputs to block 212 include: (1) filtered red and IR signals and age, (2) calibration coefficients, and (3) response mode (e.g., user speed settings). Outputs from block 212 include an averaging weight for ratio-of-ratios calculation. The averaging weight is used as an input to block 214 along with filtered IR and Red waveforms to calculate averaged ratio of ratios and age.

Block 216 represents operations that calculate oxygen saturation. Saturation is calculated using an algorithm with the calibration coefficients and averaged ratio of ratios. Inputs to block 116 include: (1) Averaged Ratio-of-Ratios, and (2) calibration coefficients. An output from block 216 is the oxygen saturation value.

II. Pulse Rate Calculation

Block 218 low pass filters and ensemble averages the signal(s) conditioned by block 202, for the pulse rate identification. The weights for the low pass filter are determined by the Signal Metrics block 206. The signal is also ensemble averaged (this attenuates frequencies other than those of interest near the pulse rate and its harmonics), with the ensemble averaging filter weights also determined by Signal Metrics block 206. Less weight is assigned if the signal is flagged as degraded. More weight is assigned if the signal is flagged as arrhythmic because ensemble-averaging is not appropriate during arrhythmia. Red and IR are processed separately, but with the same filtering weights. The filtering is delayed (e.g., approximately one second) to allow the signal metrics to be calculated first.

The filters use continuously variable weights. If samples are not to be ensemble-averaged, then the weighting for the previous filtered samples is set to zero in the weighted average, and the new samples are still processed through the signal processing algorithm. This block (block 218) tracks the age of the signal and/or the accumulated amount of filtering (sum of response times and delays in processing). Too old a result will be flagged (if good pulses haven't been detected for awhile). Inputs to block 218 include: (1) pre-processed red and IR signals, (2) average pulse period, (3) lowpass filter weights and ensemble averaging filter weights, (4) ECG triggers, if available, and (5) IR fundamental, for zero-crossing triggers. Outputs from block 218 include: (1) filtered red and IR signals and (2) age.

Block 220, or the Filtered Pulse Identification and Qualification block, calculates the pulse periods from the filtered waveforms, and its results are used only when a pulse is disqualified by block 204. Inputs to block 220 include: (1) filtered red and IR signals and age, (2) average pulse period, (3) front end ID or noise floor, (4) and the kind or type of sensor that is used to detect the IR and Red energies. Output from block 220 includes qualified pulse periods and age.

Block 222, or the Average Pulse Periods and Calculate Pulse Rate block, calculates the pulse rate and average pulse period. This block (block 222) receives qualified pulse periods and age as inputs and provides (1) average pulse period and (2) pulse rate as outputs.

III. Venous Pulsation

Block 224, or the Detect Venous Pulsation block receives as inputs the pre-processed red and IR signals and age from Block 202, and pulse rate and provides an indication of venous pulsation as an output. Block 224 also provides an IR fundamental waveform in the time domain using a single-tooth comb filter which is output to the Ensemble Averaging filters (e.g., block 210 and 218). Inputs to block 224 include: (1) filtered red and IR signals and age and (2) pulse rate. Outputs from block 124 include: an indication of venous pulsation and IR fundamental. In one embodiment, block 224 measures the "openness" of an IR-Red Lissajous plot to determine the whether a flag (e.g., Venous_Pulsation) should be set. The output flag (e.g., Venous_Pulsation) is updated periodically (e.g., every second). In addition, the IR fundamental waveform is output to the Ensemble Averaging filters.

IV. Sensor Off

Block 226, or the Detect Sensor-Off and Loss of Pulse Amplitude block, uses a pre-trained neural net to determine whether the sensor is off the surface of the blood-perfused tissue, for example, of a patient. The inputs to the neural net are metrics that quantify several aspects of the behavior of the IR and Red values over the last several seconds. Samples are ignored by many of the system 200's subsystems while the signal state is either not indicative of a pulse being present, or indicative that a sensor is not on a monitoring site (e.g., Pulse Present, Disconnect, Pulse Lost, Sensor May be Off, and Sensor Off). Inputs to block 226 include: (1) signal quality metrics, and (2) the oximeter's LED brightness, amplifier gain, and (3) an ID indicating the oximeter's hardware configuration. Outputs from block 226 include a signal state including sensor-off indication.

In the architecture 200 described above, the function of block 226, Pulse lost and Pulse Search indications, may be derived using information from several parts of the signal processing architecture. In addition, the signal processing architecture will not use the received IR and red waveforms to compute oxygen saturation or pulse rate if a valid sensor is not connected, or if the Sensor-Off or Loss of Pulse Amplitude are detected by the signal processing architecture.

The brief description of an embodiment of a pulse oximeter signal processing architecture in accordance with the present invention, set forth above, serves as a basis for describing the methods and devices that are directed towards detecting the presence or absence of venous or mixed venous and arterial pulsation in a blood perfused tissue, as is generally indicated by block 224 above.

Venous pulsation is an undesirable artifact in pulse oximetry. Venous pulsation is particularly common on the head or forehead, where the vascular anatomy lacks valves to prevent venous blood from backing up and pooling. Venous pulsation may be caused by the patient's medical condition, or during surgical interventions that interfere with venous return. The effects of venous pulsation may include: 1) oxygen saturation (e.g., $SpO_2$) readings reflecting a mix of venous and arterial blood, which would be substantially lower than the arterial oxygen saturation, thus resulting in incorrectly low oxygen saturation measurements, and 2) pulse rate readings that are double or even triple the patient's pulse rate, due to the prominent harmonics in the venous pressure wave. In addition, in extreme cases, it is possible that an oximeter would fail to acquire oxygen saturation and/or pulse rate measurements.

Unlike motion artifacts that may not be present at all times, (e.g., they come and go), venous pulsation can continue uninterrupted for hours. While the side effects of venous pulsation are highly visible to the clinician, their cause may not be. Venous pulsation at the site of an oximetry sensor may be mitigated by applying pressure to the site, such as with a headband.

The embodiments of the present invention provide methodologies, including software-based methods for detecting the venous pulsation artifact. The detection of the presence of venous pulsation enables an oximeter to display a troubleshooting message to a clinician, who could then address and/or correct the problem.

Mixed venous and arterial pulses may be distinguished from arterial pulses due to the following properties, described below. First, venous blood has a lower saturation than arterial blood. Normoxic subjects (i.e., healthy subjects breathing air at sea level) who place their head significantly below their heart may readily create $SpO_2$ readings near 80% at the forehead if no pressure is applied to the sensor site. Second, the venous pulse occurs after the arterial pulse, and has a different shape.

Figure 3A:
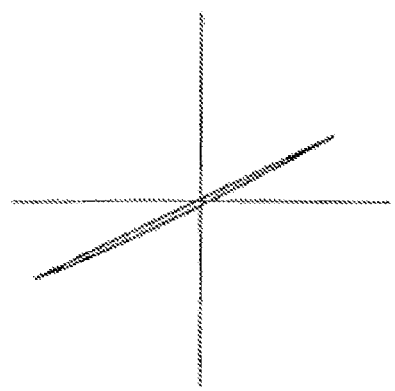
FIGS. 3A-B are exemplary x-y, or Lissajous, plots of AC-coupled IR and Red pulse waveforms plotted against one another, showing in-phase (FIG. 3A) and out of phase (FIG. 3B) IR and Red pulse waveforms.
Figure 3B:
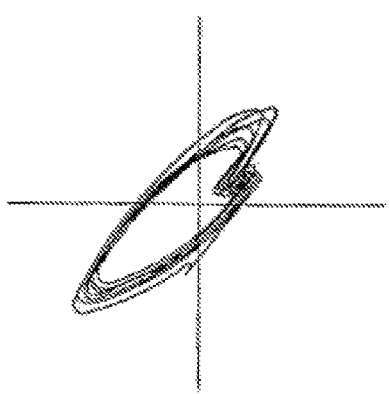

Due to these properties, the IR and red waveforms will have a significant and persistent phase difference if they include venous pulsation, as illustrated by the Lissajous plot of FIG. 3B, which resembles a fairly open ellipse. Shown in FIGS. 3A-B are IR and Red waveforms that are AC-coupled and plotted in an x-y plot, with the IR waveform on the x-axis, and the Red waveform on the y-axis. Note that the trace of FIG. 3B does not go through the origin. On the other hand, the IR and Red waveforms will be in-phase if they only include arterial pulses, as illustrated by the Lissajous plot of FIG. 3A. Other artifacts, such as motion and noise may add out-of-phase components whose phase relationship and frequency content is unstable, and not as persistent as the venous pulsation induced phase difference.

A waveform that is better suited for detecting phase differences between IR and Red waveforms is one that that contains just the waveform corresponding to the fundamental of the pulse rate, such as may be produced by an appropriate filter. Such a waveform is better suited for detecting phase differences between the IR and Red waveform that are of vascular origin.

In one embodiment, the detection of the presence of venous pulsation involves detecting persistent phase differences between the IR and Red waveforms. As set forth above, preferably the detection of the phase difference, involves the detection of the phase difference between the IR and Red waveforms that have been filtered so as to contain just frequencies at or near the algorithm's pulse-rate or harmonics. Various techniques for detecting a persistent phase difference are described below. Using one or a combination of these techniques, one embodiment of the present invention for detecting the presence of venous pulsation includes an algorithm that will:

1. AC-couple the IR and Red waveforms, and preferably filter them so as to pass only frequencies at or near the pulse rate.
2. Over a time-window of at least one complete pulse, quantify the phase difference by quantifying the "openness of the ellipse" as (minimum distance from the origin)/(maximum distance from the x-axis). Alternatively the denominator of this ratio may be the maximum distance from the origin. A longer time-window will increase the likelihood that motion artifact or Gaussian noise would eventually produce samples near the origin, and reduce the likelihood of falsely reporting venous pulsation.
3. Integrate the difference between this open-ellipse metric and a threshold. The threshold controls how open the ellipse must be to eventually notify the user of venous pulsation. The threshold preferably varies with the calculated $SpO_2$, because venous pulsation is less likely to be occurring if high $SpO_2$ values are being calculated.
4. If desired, to control how long venous pulsation must persist before notifying the user, clip the integral at pre-determined high and/or low limits, and report venous pulsation whenever a predetermined integral threshold in between the high and/or low limits is exceeded.

The description below, discloses how the "how open is the ellipse" metric is quantified. The metric is quantified as follows:

$$\text{Open\_Lissajous\_Axis\_Ratio}_t = \sqrt{\frac{\min((IR_t^2 + Red_t^2), (IR_{t-1}^2 + Red_{t-1}^2) \ldots (IR_{t-N+1}^2 + Red_{t-N+1}^2))}{\max(IR_t^2, IR_{t-1}^2 \ldots IR_{t-N+1}^2)}}$$

Where IR and Red refer to waveforms that have been processed per step 1 above, and N denotes the number of samples in the time-window.

In one embodiment, this metric is computed periodically (e.g., every second) from the most recent time window (e.g., four seconds) of data. It therefore covers a window of about several pulses. A preferred time window (e.g., four-second window) assures that the waveforms have multiple pulse periods in which to come close to the origin if the waveforms are actually in-phase. An alternate embodiment of this metric involves only using the Red data in the denominator. The inclusion of the Red data only in the numerator makes this metric more sensitive to out-of-phase waveforms at low saturations, where the Red modulation is larger, than at high saturations.

Because this ratio may be fairly noisy, it may be filtered, clipped and integrated before being used to announce the presence or absence of venous pulsation. The filtering, clipping and integration are described below, such that:

$$w = \min\left[\frac{0.005}{|\text{Open\_Lissajous\_Axis\_Ratio} - \text{Open\_Lissajous\_Axis\_Ratio}'|}, 1.0\right]$$

Filt_Open_Lissajous_Axis_Ratio=$w$*Open_Lissajous_Axis_Ratio+(1−$w$)*Filt_Open_Lissajous_Axis_Ratio' where ' denotes the value from one second ago.

Filt_Open_Lissajous_Axis_Ratio=min(Filt_Open_Lissajous_Axis_Ratio,0.3)
Open_Lissajous_Threshold=max(0.06, 0.06+ 0.5*(Saturation−90%))
Venous_Pulsation_Integral=Venous_Pulsation_Integral'+Filt_Open_Lissajous_Axis_Ratio−Open_Lissajous_Threshold Venous_Pulsation_Integral=min (2.0, max(0, Venous_Pulsation_Integral)), where:
Saturation is the oxygen saturation value.
Open_Lissajous_Threshold is the threshold defined above in step 3 of the algorithm.

In one embodiment, using the above approach, venous pulsation is reported if Venous_Pulsation_Integral is at least 1.0.

The threshold and weights in the above equations are developed empirically, and may change depending on various conditions. It is preferred that this venous pulsation detection algorithm has a response time of tens of seconds, depending on how rapidly the integral changes. This response time is adequate for the clinician's needs, as the body positions and circulatory conditions that create venous pulsation at the sensor site are not likely to change much faster than this. However, the response time can be changed to accommodate likely changes in body positions and/or circulatory conditions that create venous pulsation at the sensor site.

In addition to the technique described above for quantifying a phase difference, many alternative techniques of detecting a persistent phase difference in accordance with the present invention are also available. For instance, the phase difference may be quantified by analyzing the cross-correlation function of the two waveforms as a function of a delay interval between them. Or the phase difference may be quantified in the frequency domain by subtracting the phases of the waveforms at a given frequency. One way to subtract the phases of two complex numbers, without having to directly compute inverse trigonometric functions, is by taking their complex conjugate, and dividing by the product of their magnitudes. Or alternatively, a persistent phase-difference may be detected at a harmonic of the pulse rate, in place of, or in combination with its fundamental.

Figure 4:
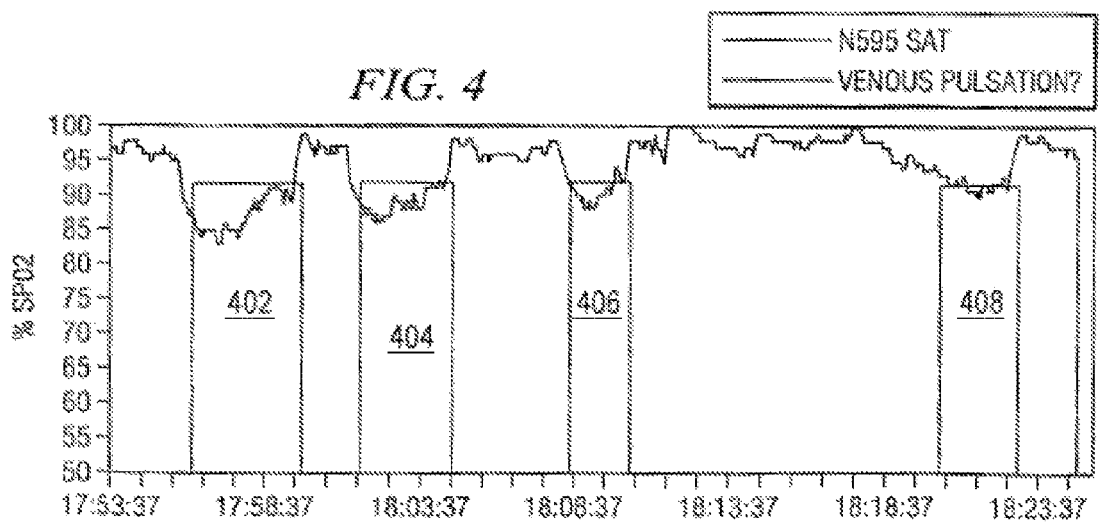
FIG. 4 is a plot of % $SpO_2$ vs. Time (hr.:min.:sec.) showing periods of venous pulsation during normoxia in Trendelenburg position (i.e., a supine position on the operating table, which is inclined at varying angles so that the pelvis is higher than the head; used during and after operations in the pelvis or for shock).

FIG. 4, which is s a plot 300 of % $SpO_2$ vs. Time (hr.:min.:sec.) showing periods of venous pulsation during normoxia in a Trendelenburg position (i.e., a supine position on the operating table, which is inclined at varying angles so that the pelvis is higher than the head; used during and after operations in the pelvis or for shock) shows that the method in accordance with the embodiments of the present invention detects all four episodes of venous pulsation created by deliberately placing a normoxic volunteer in a Trendelenburg position. The first three episodes 402, 404, and 406 were created without a headband, and venous pulsation was detected in 15-25 seconds. The final episode 408 was created with a headband in place, so that venous pulsation developed more gradually and was announced in about one minute.

A pulse oximeter having a venous pulsation detection and notification system in accordance with the embodiments of the present invention is able to identify and notify a clinician of a majority of the low (e.g., 80s-low 90s) $SpO_2$ readings as those possibly caused by venous pulsations, so that a clinician can take appropriate corrective measures, such as tightening a headband that holds an oximeter sensor against a patient's forehead. Likewise, a pulse oximeter having a venous pulsation detection and notification system in accordance with the embodiments of the present invention is able to, during a desaturation event (i.e. $SpO_2$ less than 50%), not provide an indication of a venous pulsation event, and thus help a clinician be certain that the desaturation is real event.

Accordingly, as will be understood by those of skill in the art, the present invention which is related to detecting the presence of venous or mixed venous and arterial blood pulsation is tissue, may be embodied in other specific forms without departing from the essential characteristics thereof. For example, while the present embodiments have been described in the time-domain, frequency-based methods are equally relevant to the embodiments of the present invention. Accordingly, the foregoing disclosure is intended to be illustrative, but not limiting, of the scope of the invention, which is set forth in the following claims.

What is claimed is:

1. A method of detecting the presence of mixed venous and arterial blood pulsation in tissue, comprising:
receiving first and second electromagnetic radiation signals from a blood perfused tissue portion corresponding to infrared and red wavelengths of light;
obtaining a measure of a persistent phase difference between the first and second electromagnetic radiation signals;
comparing the measure with a threshold;
detecting the presence or absence of venous pulsation using the comparison; and
indicating the presence of venous pulsation to a caregiver if venous pulsation is present.

2. The method of claim 1, comprising filtering the first and second electromagnetic radiation signals before the obtaining the measure, to pass portions of the first and second electromagnetic radiation signals having frequencies at or near the pulse rate or harmonics of the pulse rate of the blood perfused tissue.

3. The method of claim 1, wherein the obtaining the measure of the phase difference comprises integrating the measure of the phase difference over a time period.

4. The method of claim 1, wherein the obtaining the measure of the phase difference comprises obtaining a measure of the openness of an ellipse on a Lissajous plot formed by comparing the first electromagnetic radiation signal against the second electromagnetic radiation signal.

5. The method of claim 1, wherein the obtaining the measure of the phase difference comprises analyzing a cross-correlation function of the first and second electromagnetic radiation signals, as a function of a delay interval between them.

6. The method of claim 1, wherein the obtaining the measure of the phase difference comprises a frequency domain analysis and subtracting the phases of the first and second electromagnetic radiation signals at a frequency.

7. The method of claim 6, wherein the subtracting the phases of the first and second electromagnetic radiation signals comprises taking the complex conjugate of the first and second electromagnetic radiation signals, and dividing the complex conjugate by the product of the magnitudes of the first and second electromagnetic radiation signals.

8. The method of claim 1, wherein the obtaining the measure of the phase difference comprises obtaining the measure of the phase difference at or near a fundamental pulse rate of the blood perfused tissue.

9. The method of claim 1, wherein the obtaining the measure of the phase difference comprises obtaining the measure of the phase difference at or near a harmonic of a pulse rate of the blood perfused tissue.

10. The method of claim 1, wherein the obtaining the measure of the phase difference comprises obtaining the measure of the phase difference at or near a fundamental or at or near a harmonic of a pulse rate of the blood perfused tissue.

11. A device for detecting the presence of mixed venous and arterial blood pulsation in tissue, comprising:
   means for receiving first and second electromagnetic radiation signals from a blood perfused tissue portion corresponding to infrared and red wavelengths of light;
   means for obtaining a measure of a persistent phase difference between the first and second electromagnetic radiation signals;
   means for comparing the measure with a threshold value to form a comparison;
   means for detecting the presence or absence of venous pulsation using the comparison; and
   means for indicating the presence of venous pulsation to a caregiver when venous pulsation is present.

12. The device of claim 11, comprising a filter configured for filtering the first and second electromagnetic radiation signals before obtaining the measure, to pass portions of the first and second electromagnetic radiation signals having frequencies at or near the pulse rate or harmonics of the pulse rate of the blood perfused tissue.

13. The device of claim 11, wherein the means for obtaining the measure of the phase difference comprises means for integrating the measure of the phase difference over a time period.

14. The device of claim 11, wherein the means for obtaining the measure of the phase difference is configured for obtaining a measure of the openness of an ellipse on a Lissajous plot formed by comparing the first electromagnetic radiation signal against the second electromagnetic radiation signal.

15. The device of claim 11, wherein the means for obtaining the measure of the phase difference is configured for analyzing a cross-correlation function of the first and second electromagnetic radiation signals, as a function of a delay interval between them.

16. The device of claim 11, wherein the means for obtaining the measure of the phase difference is configured for a frequency domain analysis and for subtracting the phases of the first and second electromagnetic radiation signals at a frequency.

17. The device of claim 16, wherein the means for subtracting the phases of the first and second electromagnetic radiation signals is configured for taking the complex conjugate of the first and second electromagnetic radiation signals, and dividing the complex conjugate by the product of the magnitudes of the first and second electromagnetic radiation signals.

18. The device of claim 11, wherein the means for obtaining the measure of the phase difference is configured for obtaining the measure of the phase difference at or near a fundamental or at or near a harmonic of a pulse rate of the blood perfused tissue.

* * * * *